United States Patent [19]

VandenBerg

[11] Patent Number: Plant 7,759

[45] Date of Patent: Dec. 31, 1991

[54] CHRYSANTHEMUM PLANT NAMED BLONDELLE

[75] Inventor: Cornelis P. VandenBerg, Salinas, Calif.

[73] Assignee: Yoder Brothers, Inc., Barberton, Ohio

[21] Appl. No.: 565,707

[22] Filed: Aug. 13, 1990

[51] Int. Cl.[5] ..... A01H 5/00

[52] U.S. Cl. ..... Plt./74

[58] Field of Search ..... Plt./74, 82.2

*Primary Examiner*—Howard J. Locker

*Attorney, Agent, or Firm*—Foley & Lardner

[57] ABSTRACT

A Chrysanthemum plant named Blondelle particularly characterized by its flat capitulum form; daisy capitulum type; yellow ray floret color; diameter across face of capitulum of 32 to 38 mm. when fully opened when grown as a pinched spray pot mum; very floriferous with excellent display of many small flowers; photoperiodic response to short days of 48 to 54 days; medium plant height of 20 to 28 cm. when grown as a pinched pot mum; small dark green foliage; spreading and prolific branching pattern; and excellent tolerance to high temperatures for bud initiation and flower development.

3 Drawing Sheets

The present invention comprises a new and distinct cultivar of Chrysanthemum, botanically known as *Dendranthema grandiflora*, and referred to by the cultivar name Blondella.

Blondella, identified as 86-812001, was originated from a cross made by Cornelis P. VandenBerg in a controlled breeding program in Salinas, Calif., in 1986.

The female parent of Blondelle was the cultivar idenified as Cartago, disclosed in U.S. Plant Pat. No. 7,211. Cartago can be described as a flat daisy having bright yellow ray florets, uniform eight week response, diameter up to 7 cm. and short plant height.

The male parent of Blondelle was an unnamed seedling, identified as 83-S58005, and described as a white spooned daisy spray pot mum having many very small flowers, a flowering response to short days of 53 to 62 days under normal conditions, a plant height of 23 to 28 cm. with 18 to 20 long days after sticking unrooted cuttings and 0 to 1 applications of 2500 ppm B-9 SP, breaking action of 6 to 8 breaks per plant after pinch, and a wide spread habit. The male parent was discarded from the program on June 27, 1986, and no further information is available on this parent.

Blondelle was discovered and selected as one flowering plant within the progeny of the stated cross by Cornelis P. VandenBerg in March 1987, in a controlled environment in Salinas, Calif.

The first act of asexual reproduction of Blondelle was accomplished when vegetative cuttings were taken from the initial selection in April 1987 in a controlled environment in Salinas, Calif., by technicians working under the supervision of Cornelis P. VandenBerg.

Horticultural examination of controlled flowerings of successive plantings has shown that the unique combination of characteristics as herein disclosed for Blondelle are firmly fixed and are retained through successive generations of asexual reproduction.

Blondelle has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The high temperature tolerance was determined in a controlled environment in Salinas, Calif., where temperatures were maintained at 35 degrees Celsius during the day and 24 degrees Celsius during the night for the duration of the crop. Under such temperatures many Chrysanthemum cultivars will exhibit a severely delayed flowering response, often with very uneven flowering. Blondelle under these temperatures showed no delay in flowering response, and was very uniform in flowering.

The following traits have been repeatedly observed and are determined to be basic characteristics of Blondelle, which, in combination, distinguish this Chrysanthemum as a new and distinct cultivar:

1. Flat capitulum form.
2. Daisy capitulum type.
3. Yellow ray floret color.
4. Diameter across face of capitulum of 32 to 38 mm. when fully opened, when grown as a pinched spray pot mum.
5. Very floriferous with excellent display of many small flowers.
6. Photoperiodic flowering response to short days of 48 to 54 days.
7. Plant height, with 14 to 16 long days after sticking unrooted cuttings, and with 1 to 2 applications of 2500 ppm B-9 SP, ranges from 20 to 28 cm. when grown as a pinched pot mum with 4 cuttings in a 15 cm. pot.
8. Small, dark green foliage.
9. Branching pattern is spreading and prolific, each plant having 5 to 7 laterals after pinch.
10. Excellent tolerance to high temperatures for bud initiation and flower development.

The accompanying photographic drawings show typical inflorescence and leaf characteristics of Blondelle, with the colors being as nearly true as possible with illustrations of this type.

Sheet 1 is a color photograph of Blondelle grown as a pinched spray pot mum with 4 cuttings in a 15 cm. pot.

Sheet 2 is a black and white photograph of three views of the inflorescence of Blondelle.

Sheet 3 is a black and white photograph showing the upper and under sides of the leaves of Blondelle at three stages of development (mature, intermediate and immature).

Sheets 2 and 3 include a measuring tape in centimeters, thereby illustrating the dimensions of the flowers and leaves.

Of the commercial cultivars known to the inventors, the most similar in comparison to Blondelle is the cultivar Alouette, disclosed in my pending Plant patent application Ser. No. 07/409,455, now U.S. Plant Pat. No. 7,468. Reference is made to attached Chart A, which compares certain characteristics of Blondelle to the same characteristics of Alouette.

Similar traits are capitulum form and type, controlled flowering response, plant height and high temperature tolerance. The ray floret color of Blondelle is a medium yellow (3B-C), while Alouette has a much deeper yellow ray floret color (9A-B), with the underside of the ray florets and the buds being red-bronze. Blondelle has a smaller flower and an average of one lateral less after pinch when compared with Alouette.

When compared with both parents, Blondelle has a faster flowering response than either parent. High temperature tolerance of Cartago is marginal, while the high temperature tolerance of the male parent was never determined.

In the following description color references are made to The Royal Horticultural Society Colour Chart. The color values were determined on plant material grown as a pinched spray pot mum in Salinas, Calif. on Apr. 30, 1990.

Classification:

*Botanical.*—*Dendranthema grandiflora* cv Blondelle.

*Commercial.*—Daisy spray pot mum.

INFLORESCENCE

A. Capitulum:

*Form.*—Flat.

*Type.*—Daisy.

*Diameter across face.*—32 to 38 mm. when fully opened.

B. Corolla of ray florets:

*Color (general tonality from a distance of three meters).*—Yellow.

*Color.*—Upper surface: 3B to 3C. Under surface: 3C to 3D.

*Shape.*—Straight, oblong, slightly ribbed. Apex slightly indented.

C. Corolla of disc florets:

*Color (mature).*—6B.

*Color (immature).*—3A, overlaid with 144B.

D. Reproductive organs:

*Androecium.*—Present on disc florets only; moderate pollen.

*Gynoecium.*—Present on both ray and disc florets.

PLANT

A. General appearance:

*Height.*—20 to 28 cm. when grown as a pinched pot mum in a 15 cm. pot with 14 to 16 long days after direct sticking of unrooted cuttings and 1 to 2 applications of 2500 ppm B-9 SP.

*Branching pattern.*—Spreading and prolific, with 5 to 7 laterals after pinch.

B. Foliage:

*Color (upper surface).*—147A.

*Color (under surface).*—147B.

*Shape.*—See photograph.

CHART A
COMPARISON OF BLONDELLE AND ALOUETTE

| CHARACTERISTIC | BLONDELLE | ALOUETTE |
|---|---|---|
| Ray floret color | Yellow (3B–C) | Deep yellow (9A–B) with red-bronze underside |
| Capitulum form and type | Flat daisy | Flat daisy |
| Spray formation | Terminal | Terminal |
| Diameter across face of capitulum | 32 to 38 mm. | 38 to 45 mm. |
| Flowering response | 48 to 54 days | 47 to 55 days |
| Plant height with 14 to 16 long days | 20 to 28 cm. | 20 to 28 cm. |
| Branching pattern | Spreading 5 to 7 laterals | Spreading 6 to 8 laterals |
| High temperature tolerance | Excellent | Excellent |

COMPARISONS MADE OF PLANTS GROWN AS PINCHED SPRAY POT MUMS IN SALINAS, CALIFORNIA

I claim:

1. A new and distinct Chrysanthemum plant named Blondelle, as described and illustrated.

* * * * *

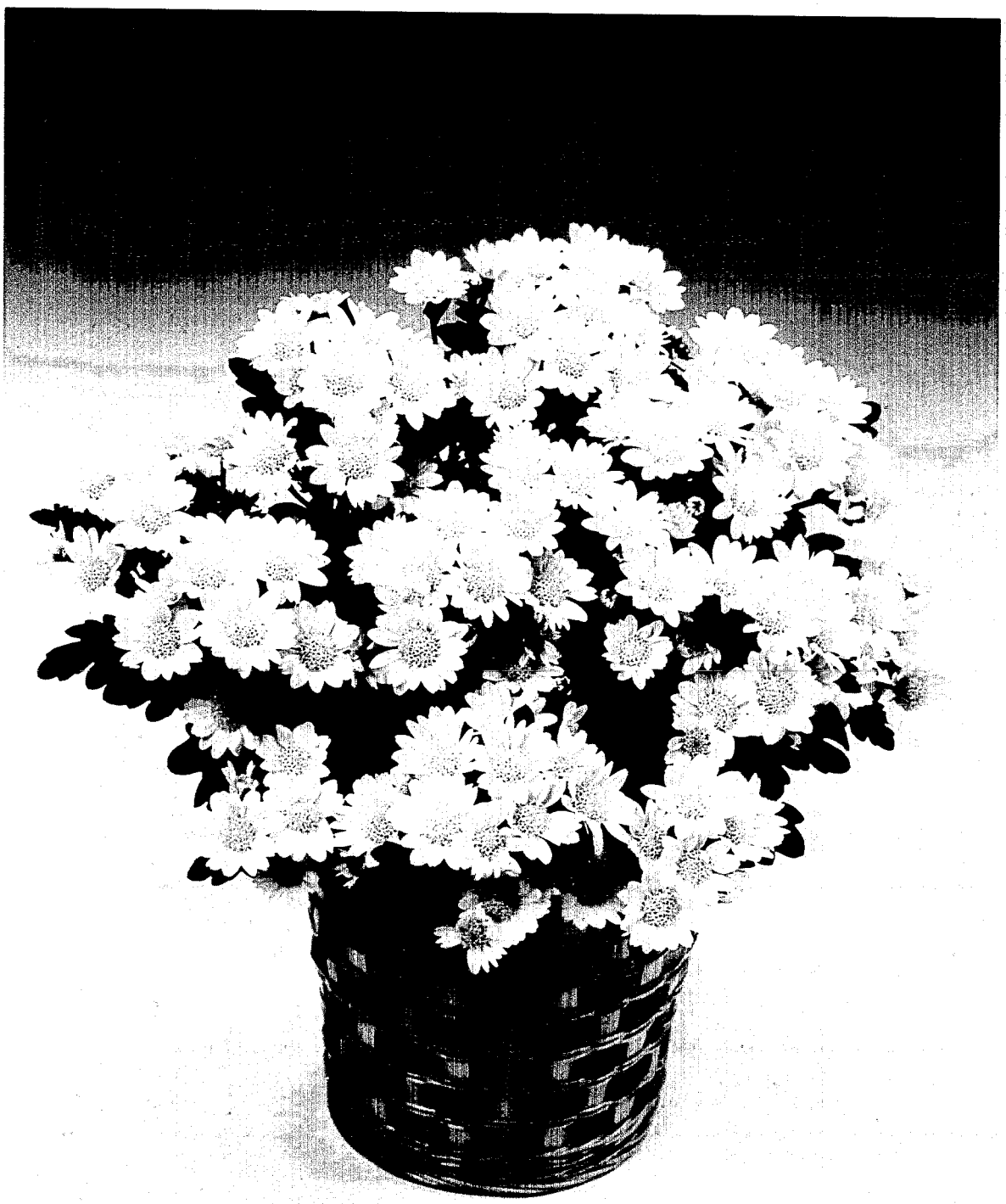

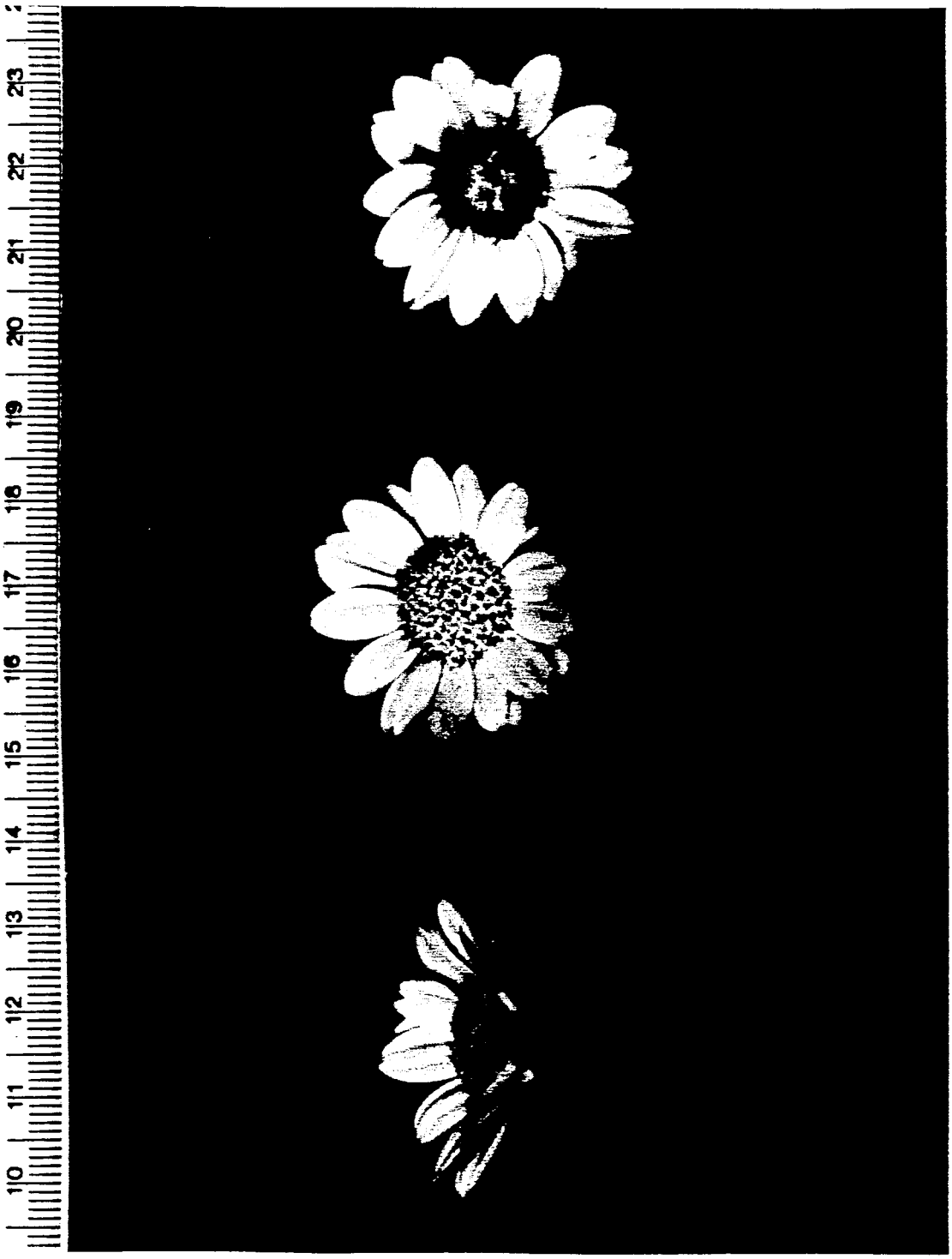
10
11
12
13
14
15
16
17
18
19
20
21
22
23

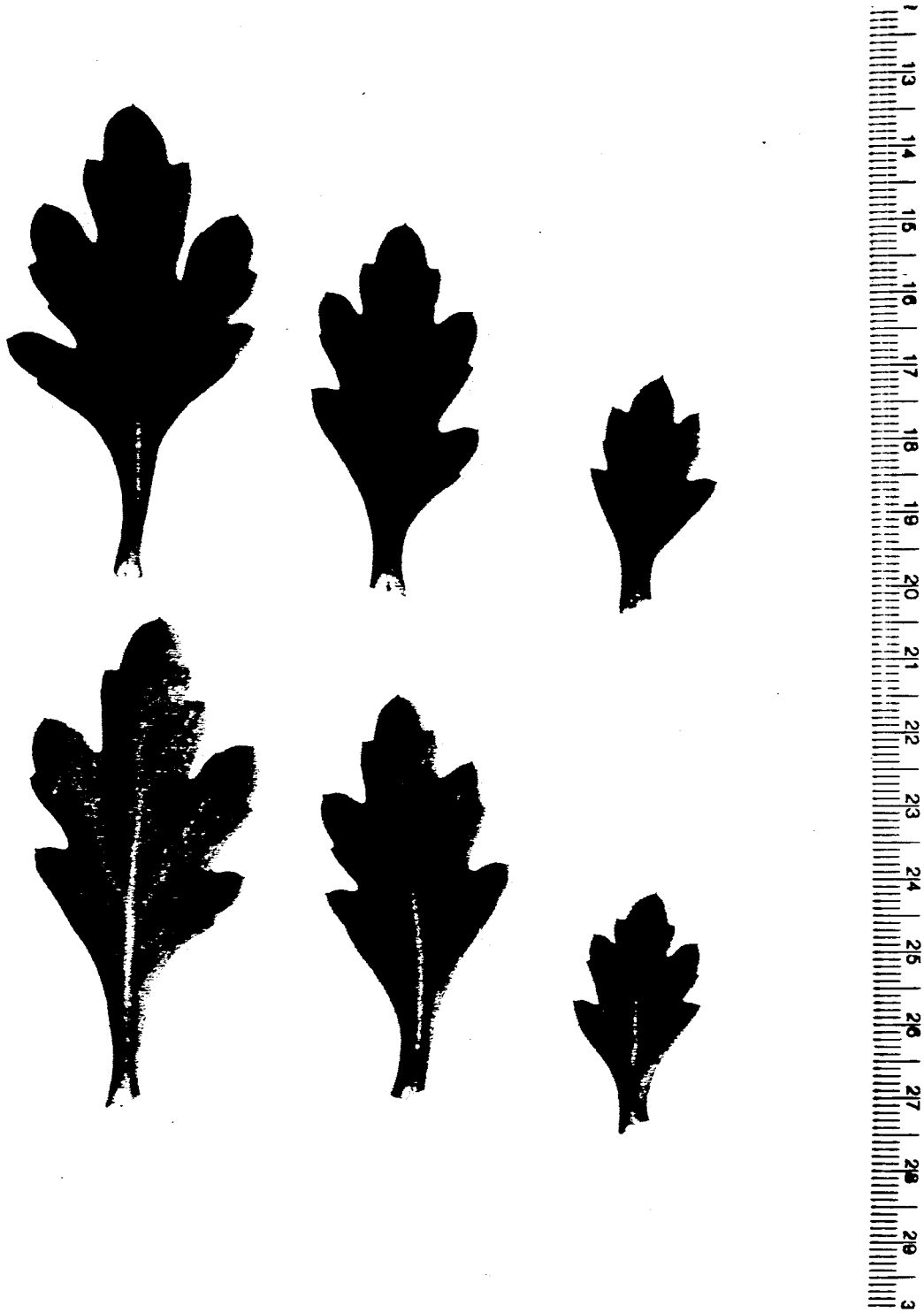

UNITED STATES PATENT AND TRADEMARK OFFICE

CERTIFICATE OF CORRECTION

PATENT NO. : PP 7,759

DATED : December 31, 1991

INVENTOR(S) : Cornelis P. VandenBerg

It is certified that error appears in the above-identified patent and that said Letters Patent is hereby corrected as shown below:

Column 1, line 4, "Blondella" should read --Blondelle--.

Column 1, line 5, "Blondella" should read --Blondelle--.

Column 1, line 8, "ideni-" should read --identi---.

Signed and Sealed this

Twenty-sixth Day of October, 1993

*Attest:*

*Attesting Officer*

Bruce Lehman

BRUCE LEHMAN

*Commissioner of Patents and Trademarks*